(12) United States Patent
Wang et al.

(10) Patent No.: US 9,953,734 B2
(45) Date of Patent: Apr. 24, 2018

(54) MICROSTRUCTURE MANUFACTURING METHOD

(71) Applicant: CANON KABUSHIKI KAISHA, Tokyo (JP)

(72) Inventors: Shinan Wang, Kashiwa (JP); Takashi Nakamura, Yokohama (JP); Takayuki Teshima, Yokohama (JP); Yutaka Setomoto, Tokyo (JP); Shinichiro Watanabe, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/007,773

(22) Filed: Jan. 27, 2016

(65) Prior Publication Data

US 2016/0163408 A1   Jun. 9, 2016

Related U.S. Application Data

(60) Division of application No. 14/539,787, filed on Nov. 12, 2014, now abandoned, which is a continuation of
(Continued)

(30) Foreign Application Priority Data

Jan. 8, 2010   (JP) ................................ 2010-003327
Nov. 29, 2010  (JP) ................................ 2010-265093

(51) Int. Cl.
*G21K 1/06*   (2006.01)
*G01T 1/29*   (2006.01)
(Continued)

(52) U.S. Cl.
CPC ............ *G21K 1/06* (2013.01); *B81C 1/00619* (2013.01); *G01N 23/20075* (2013.01);
(Continued)

(58) Field of Classification Search
CPC .......................................... G02B 5/18–5/1895
See application file for complete search history.

(56) References Cited

U.S. PATENT DOCUMENTS 8,593,732 B1 *  11/2013  Greiner .................... G02B 5/18
                                                 359/485.05
2010/0248449 A1 *  9/2010  Hildreth ............. B81C 1/00071
                                                 438/460
(Continued)

FOREIGN PATENT DOCUMENTS

JP      11-231099 A      8/1999
JP      H11231099 A     8/1999
(Continued)

*Primary Examiner* — Casey Bryant
(74) *Attorney, Agent, or Firm* — Canon U.S.A., Inc. IP Division (57) ABSTRACT

A microstructure manufacturing method includes forming a first insulating film on an Si substrate, exposing an Si surface by removing a part of the first insulating film, forming a recessed portion by etching the Si substrate from the exposed Si surface, forming a second insulating film on a sidewall and a bottom of the recessed portion, forming an Si exposed surface by removing at least a part of the second insulating film formed on the bottom of the recessed portion, and filling the recessed portion with a metal from the Si exposed surface by electrolytic plating.

10 Claims, 7 Drawing Sheets

Related U.S. Application Data application No. 12/986,015, filed on Jan. 6, 2011, now Pat. No. 8,895,934.

(51) Int. Cl.
  *B81C 1/00* (2006.01)
  *H01L 21/311* (2006.01)
  *H01L 21/3205* (2006.01)
  *G01N 23/20* (2018.01)

(52) U.S. Cl.
  CPC ........ *G01T 1/295* (2013.01); *H01L 21/31111* (2013.01); *H01L 21/32051* (2013.01)

(56) References Cited

U.S. PATENT DOCUMENTS

| | | | | |
|---|---|---|---|---|
| 2011/0013743 A1* | 1/2011 | Nakamura | ............... | A61B 6/06 378/19 |
| 2011/0052800 A1* | 3/2011 | Setomoto | ......... | B29D 11/00769 427/162 |
| 2011/0194673 A1* | 8/2011 | Teshima | .................. | G21K 1/06 378/62 |
| 2013/0051530 A1* | 2/2013 | Nepomnishy | .......... | G21K 1/025 378/85 |
| 2013/0052826 A1* | 2/2013 | Nepomnishy | .......... | G21K 1/025 438/694 |
| 2015/0376798 A1* | 12/2015 | Sakdinawat | ............. | G21K 1/06 216/51 |
| 2016/0170102 A1* | 6/2016 | Hafner | ................ | G02B 5/1809 359/574 |

FOREIGN PATENT DOCUMENTS

| | | |
|---|---|---|
| JP | 2002-110897 A | 4/2002 |
| JP | 2002110897 A | 4/2002 |
| JP | 2004-261605 A | 9/2004 |
| JP | 2004261605 A | 9/2004 |
| JP | 2009-037023 A | 2/2009 |
| JP | 2009037023 A | 2/2009 |
| JP | 2009-244260 A | 10/2009 |
| JP | 2009244260 A | 10/2009 |
| JP | 2011-157622 A | 8/2011 |

\* cited by examiner

MICROSTRUCTURE MANUFACTURING METHOD

CROSS-REFERENCE TO RELATED APPLICATIONS

This application is a Division of U.S. patent application Ser. No. 14/539,787, filed Nov. 12, 2014, which is a Continuation of U.S. patent application Ser. No. 12/986,015, filed Jan. 6, 2011, which claims priority from Japanese Patent Applications No. 2010-003327, filed Jan. 8, 2010 and No. 2010-265093, filed Nov. 29, 2010, each of which is hereby incorporated by reference herein in its entirety. U.S. patent application Ser. No. 12/986,015 has now issued as U.S. Pat. No. 8,895,934.

BACKGROUND OF THE INVENTION

Field of the Invention

The present invention relates to a method for manufacturing a microstructure, and, in particular, to a method for manufacturing a microstructure by electrolytic plating of a metal with use of a mold, especially a microstructure having a high aspect ratio.

Description of the Related Art

A micro fine structure having periodic structure, especially a high aspect ratio structure is needed in a large number of fields. For example, the X-ray absorption characteristic of a microstructure composed of gold is utilized in a nondestructive test of an object as an industrial application, and also utilized in, for example, radiography as a medical application. A microstructure in these applications forms a contrast image by utilizing an absorption difference in X-ray transmission depending on constituent elements and a density variation in an object or a biological object, and is called the X-ray absorption contrast method.

Further, the phase contrast method using a phase difference of X-ray has been researched actively since even light elements can be imaged by this method, and for example, the propagation method and the Talbot interference method has been becoming feasible in principle. Generally, the method using Talbot interference is carried out with use of an absorption grating comprised of gold having a periodic structure and large absorption of X-ray. Since it is difficult to directly manufacture a golden microstructure having a high aspect ratio ("aspect ratio" is defined as a ratio of a height or depth h and a width w of a structure (h/w)), the method of filling a mold with gold by plating is preferable as a method for manufacturing a golden absorption grating constituted by a periodic structure.

Japanese Patent Application Laid-Open No. 2007-203066 discusses a structure of an X-ray optical transmission grating for the above-described phase contrast method. Further, with the aim of solving the problem of a significant reduction in fabrication precision according to an increase in the aspect ratio of a structure, Japanese Patent Application Laid-Open No. 2007-203066 discusses a combination of partial gratings which functions as one grating.

However, Japanese Patent Application Laid-Open No. 2007-203066 does not discuss a method for manufacturing a microstructure having a high aspect ratio.

SUMMARY OF THE INVENTION

The present invention is directed to a microstructure manufacturing method enabling easy manufacturing of a metal microstructure having a high aspect ratio with a high degree of precision.

According to an aspect of the present invention, a microstructure manufacturing method includes forming a first insulating film on an Si substrate, exposing an Si surface by removing a part of the first insulating film, forming a recessed portion by etching the Si substrate from the exposed Si surface, forming a second insulating film on a sidewall and a bottom of the recessed portion, forming a Si exposed surface by removing at least a part of the second insulating film formed on the bottom of the recessed portion, and filling the recessed portion with a metal from the Si exposed surface by electrolytic plating.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

FIG. 1 illustrates a first exemplary embodiment of the microstructure manufacturing method according to the present invention. This manufacturing method is a method including forming a microstructure on one surface of an Si substrate, and forming a metal microstructure by applying electrolytic plating to the inside of the Si microstructure while using the Si microstructure as a mold.

Figure 1A:
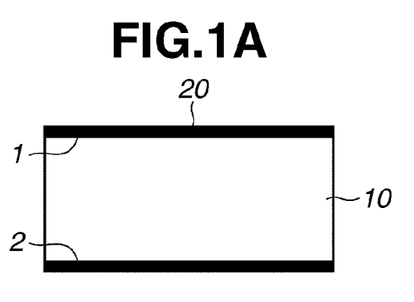
FIGS. 1A to 1G illustrate a microstructure manufacturing method according to a first exemplary embodiment of the present invention.

First, a first insulating film is formed on the front surface and the back surface of the Si substrate (first process). As illustrated in FIG. 1A, the first insulating film 20 is formed on a front surface 1 and a back surface 2 of an Si substrate 10. The size and thickness of the Si substrate 10 can be determined according to a desired microstructure. Further, the resistivity of the Si substrate 10 is 10 Ωcm or less, preferably or optimally 0.1 Ωcm or less.

The material of the first insulating film 20 is an insulating material having resistivity sufficiently high relative to the Si substrate 10. Preferably, the resistivity of the first insulating film 20 is equal to or more than ten times the resistivity of the Si substrate 10. Preferably, the first insulating film 20 can offer sufficient selectivity ratio, and can be used as a mask material in the later processing of an Si microstructure. Preferably, the material of the first insulating film 20 is, for example, $SiO_2$ or an Si nitride film. Preferably, the thickness of the first insulating film 20 is 0.1 μm or more, and 5 μm or less. Examples of $SiO_2$ film formation methods include the thermal oxidation method and the chemical vapor deposition (CVD) method. Examples of Si nitride film formation methods include the chemical vapor deposition (CVD) method. Preferably, the first insulating film 20 is formed on both of the front surface and the back surface of the substrate.

Figure 1B:
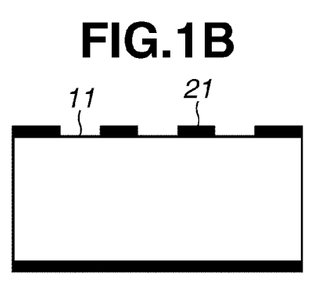

Next, the Si surface of the Si substrate is exposed by removing a part of the first insulating film on the front surface of the Si substrate (second process). As illustrated in FIG. 1B, a mask pattern 21 is formed by removing a part of the first insulating film 20, and at the same time, an Si surface 11 portion is formed by partially exposing the front surface of the Si substrate 10. The partial removal of the first insulating film 20 will be described based on the case that the material of the first insulating film 20 is $SiO_2$ by way of example. For example, after a metal film (for example, Cr) is formed on the first insulating film 20, a photoresist (for example, AZ1500: manufactured by AZ Electronic Materials Company) is applied thereon. Then, the photoresist is exposed to light for the formation of a pattern. The shape and size of the pattern is determined based on a desired metal microstructure. For example, the pattern may be constituted by a periodic structure of a square pattern, the period of which is approximately 1 μm to 100 μm and a length of one side of which is 0.5 μm to 80 μm. Then, the photoresist pattern is transferred onto the metal film by etching. The metal film etching method may be embodied by a wet etching method with use of a solution or a dry etching method such as ion sputtering and reactive gaseous plasma etching. After that, the first insulating film 20 is etched using the metal film with the pattern transferred thereon as a mask. For example, preferably, the etching of the first insulating film 20 is carried out by a dry etching method. If the first insulating film 20 is made of $SiO_2$, preferably, the etching is carried out by the dry etching method with use of $CHF_3$ plasma.

Figure 1C:
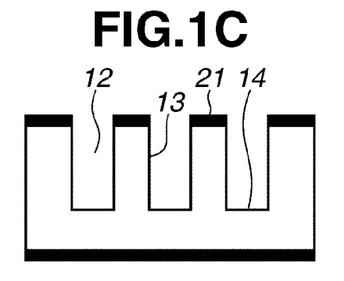

Next, the Si recessed portion is formed by etching the Si substrate from the exposed Si surface using the first insulating film on the front surface of the Si substrate as a mask (third process). As illustrated in FIG. 1C, an Si recessed portion 12 is formed by processing the Si substrate 10 from the Si surface 11 portion exposed by the partial removal of the first insulating film 20 using the pattern 21 on the first insulating film formed by the previous processing as a mask. FIG. 1C illustrates each of a sidewall 13 and a bottom 14 of the Si recessed portion 12. The method of processing the Si substrate 10 may be embodied by a wet etching method with use of a solution or a dry etching method such as ion sputtering and reactive gaseous plasma etching. Especially, out of the reactive gaseous plasma dry etching methods, reactive ion etching (RIE) is suitable for manufacturing a high aspect ratio structure. Further especially, out of RIE, Bosch process RIE, which alternately repeats etching by $SF_6$ gas and sidewall protective film deposition by $C_4F_8$ gas, is further suitable for manufacturing a high aspect ratio structure. Use of Bosch process RIE enables manufacturing of a structure having an aspect ratio of approximately 100. Desirably, if the Bosch process RIE is carried out, the sidewall protective film is removed after the RIE. The removal of the sidewall protective film can be carried out by, for example, cleaning with use of a hydro fluoro ether (HFE) solution.

Figure 1D:
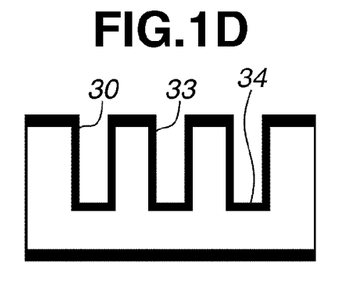

Next, a second insulating film is formed on the sidewall and the bottom of the Si recessed portion (fourth process). As illustrated in FIG. 1D, a second insulating film 30 is formed on the sidewall 13 and the bottom 14 of the Si recessed portion 12 formed by the previous processing. The material of the second insulating film 30 may be the same as or different from the material of the above-described first insulating film 20. For example, both the material of the first insulating film 20 and the material of the second insulating film 30 are $SiO_2$. Alternatively, the material of the first insulating film 20 is $SiO_2$, and the material of the second insulating film 30 is a Silicon nitride film. Alternatively, the material of the first insulating film 20 is an Si nitride film, and the material of the second insulating film 30 is $SiO_2$. The thickness of the second insulating film 30 is within the range of 5 nm to 5000 nm, preferably 10 nm to 1000 nm, most preferably 20 nm to 200 nm. The thickness of the second insulating film 30 does not necessarily have to be even throughout the Si recessed portion 12 and the region of the sidewall 13, and only have to be 10 nm or more at the thinnest portion. More preferably, the second insulating film 30 has the thinnest thickness at a portion denoted by reference numeral 34 (the bottom 14 of the Si recessed portion 12). The second insulating film 30 may be formed on a portion other than the sidewall 13 and the bottom 14 (for example, on the top portion 21 of the substrate or the back surface of the substrate).

Figure 1E:
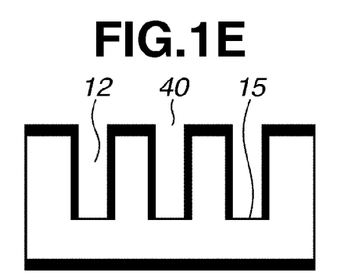
Figure 1F:
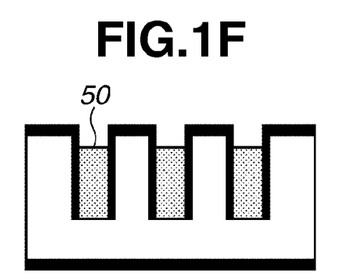
Figure 1G:
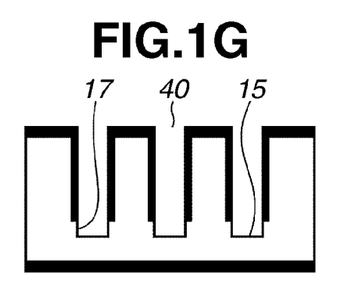

Next, the Si exposed surface is formed by at least partially removing the second insulating film formed on the bottom of the above-described Si recessed portion (fifth process). As illustrated in FIG. 1E, an Si exposed surface 15 is formed by at least partially removing the second insulating film 34 formed on the bottom 14 of the Si recessed portion 12. Preferably, the partial removal of the second insulating film 34 is carried out by a highly anisotropic dry etching method. For example, the removal of the second insulating film 34 is carried out by the ion sputtering method or the reactive gaseous plasma etching method. In such a method, since the second insulating film 34 at the bottom is preferentially removed due to the anisotropy of the etching, the second insulating film 34 can remain at the sidewall at least thinly, preventing the Si surface from being exposed at the sidewall. Further, if the insulating film on the top surface of the substrate is made to be sufficiently thicker than the second insulating film 34 on the bottom, this enables the Si surface on the top surface of the substrate to be prevented from being exposed when the second insulating film 34 is removed. If the second insulating film 34 is made of $SiO_2$, the removal thereof is preferably carried out by the dry etching method with use of $CHF_3$ plasma. The Si exposed surface 15 illustrated in FIG. 1E corresponds to the bottom 14 of the Si recessed portion. As illustrated in FIG. 1G, it is also convenient for carrying out the present exemplary embodiment to further expose a sidewall 17 of the Si recessed portion adjacent to the bottom 14 by further processing the bottom 14 after the bottom 14 is exposed, if desired. Execution of the above-described processes results in the formation of an Si mold 40 for plating.

Next, a metal microstructure is formed by filling the Si recessed portion with a metal from the above-described Si exposed surface by electrolytic plating (sixth process). As illustrated in FIG. 1F, a metal microstructure 50 is formed by electrolytic plating the inside 12 of the Si structure with a metal from the Si exposed surface 15 while using the Si mold 40 as a mold. In the Si mold 40, an exposed surface is only the surface of the bottom of the Si recessed portion which constitutes the Si exposed surface 15, and the other portions including the back surface of the substrate are all covered with the insulating film. Therefore, in the electrolytic plating, the metal can be deposited only from the Si exposed surface 15. As a result, a fine metal microstructure can be manufactured within the recessed portion 12 of the Si mold 40. The metal may be embodied by any metal enabling a formation of a microstructure by electrolytic plating, for example, preferably Au and Ni. An electrode pad for the mold side for the electrolytic plating may be formed at, for example, the periphery of the front surface of the Si substrate 10 or the back surface of the Si substrate 10. In this case, the electro pad formation method may be embodied by, for example, the method of removing the first insulating film 20 and the second insulating film 30 at an appropriate position at the periphery of the Si substrate 10 or the back surface of the Si substrate 10 to expose the surface of the Si substrate after the completion of the formation of the Si mold 40 till the process of FIG. 1E. Alternatively, for the electro pad, an Si recessed portion having an area suitable for an electro pad may be formed at an appropriate position at the periphery of the front surface of the Si substrate 10, at the same time of the formation of the Si recessed portion 12 as illustrated from FIGS. 1A to 1E.

The above-described processes of the manufacturing method may be carried out with support from the well known Micro Electro Mechanical System (MEMS) technology. Further, the present exemplary embodiment does not require additional formation of a seed electrode which would be required in an ordinary electrolytic plating process, and reduces the number of manufacturing processes. Especially, the present exemplary embodiment does not require a difficult technology for selectively forming a seed electrode at the bottom of a high aspect ratio structure, and realizes easy manufacturing.

According to the present exemplary embodiment, it is possible to manufacture a metal micro grating structure having an aspect ratio of 0.1 to 150, preferably 5 to 100, with a high degree of submicron precision.

FIGS. 2A to 2H illustrate a second exemplary embodiment according to the microstructure manufacturing method of the present invention. FIGS. 2A to 2H illustrate the second exemplary embodiment of the present invention. The following description will disclose a microstructure manufacturing method including forming microstructures on the both surfaces of an Si substrate, and forming metal microstructures in the microstructures by electrolytic plating while using the microstructures as molds.

Figure 2A:
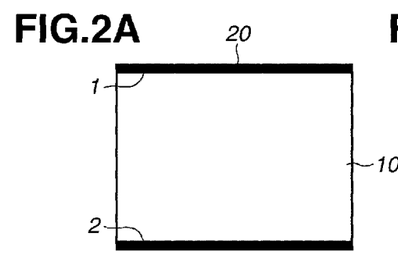
FIGS. 2A to 2H illustrate a microstructure manufacturing method according to a second exemplary embodiment of the present invention.
Figure 2B:
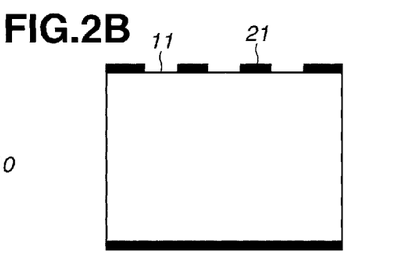
Figure 2C:
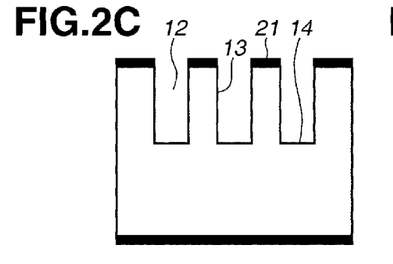

First, the first insulating film is formed on the front surface 1 and the back surface 2 of the Si substrate (first process). Next, the Si surface of the Si substrate is exposed by removing a part of the first insulating film on the front surface of the Si substrate, and then the Si recessed portion is formed on the front surface of the Si substrate by etching the Si substrate from the exposed Si surface while using the first insulating film on the front surface of the Si substrate as a mask (second process).

More specifically, as illustrated in FIGS. 2A to 2C, the Si microstructure is formed on the front surface of the Si substrate 10. The formation method therefor can be carried out in a similar manner to the method of the first exemplary embodiment as illustrated in FIGS. 1A and 1C.

Figure 2D:
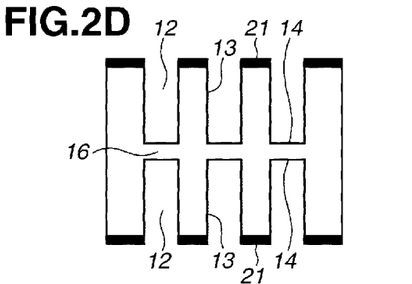

Next, the Si surface of the Si substrate is exposed by removing a part of the first insulating film on the back surface of the Si substrate, and then the Si recessed portion is formed on the back surface of the Si substrate by etching the Si substrate from the exposed Si surface while using the first insulating film on the back surface of the Si substrate as a mask (third process).

As illustrated in FIG. 2D, the Si recessed portion corresponding to the Si recessed portion formed on the front surface of the Si substrate 10 is formed on the back surface of the Si substrate 10 in a substantially mirror-symmetrical manner by applying processing from the back surface. In other words, the Si recessed portions are formed on the front surface and the back surface of the Si substrate so as to establish a mirror-symmetrical relationship therebetween. Preferably, the Si microstructure on the back surface is substantially mirror-symmetrical to the Si microstructure on the front surface as viewed in a planar figure. When a photoresist pattern is formed on the back surface, the position thereof is aligned to the Si recessed portion on the front surface of the Si substrate with use of a position alignment mark formed in advance on the front surface of the Si substrate, in order to precisely set the positional relationship between the Si recessed portions on the front surface and the back surface. On the other hand, the Si recessed portions on the front surface and the back surface do not have to have a same depth. Preferably, an intermediate layer 16, which is defined between the Si recessed portions on the front surface and the back surface, is thin. For example, the thickness of the intermediate layer 16 may be 500 μm or less, more preferably 50 μm or less. Such a dimension can be realized by determining the thickness of the Si substrate 10 in consideration of the thickness of the intermediate layer 16.

Figure 2E:
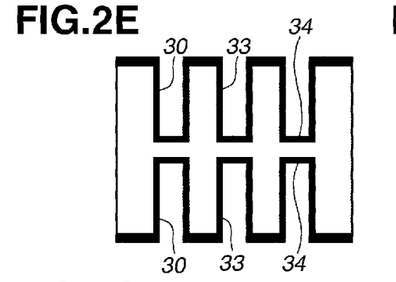

Next, the second insulating films are formed on the sidewalls and the bottoms of the Si recessed portions on the front surface and the back surface of the Si substrate (fourth process). As illustrated in FIG. 2E, the second insulating films 30 are formed on the sidewalls 13 and the bottoms 14 of the Si recessed portions 12 formed by the previous processing. At this time, the second insulating films 30 may be formed on the Si recessed portions on the front surface and the back surface either concurrently or separately. Further, the materials of the second insulating films 30 formed on the Si recessed portions on the front surface and the back surface may be either substantially similar to each other or different from each other. The details of the second insulating film 30 such as the formation method thereof and the dimension of the thickness thereof may be similar to the second insulating film 30 in the first exemplary embodiment as illustrated in FIG. 1D.

Figure 2F:
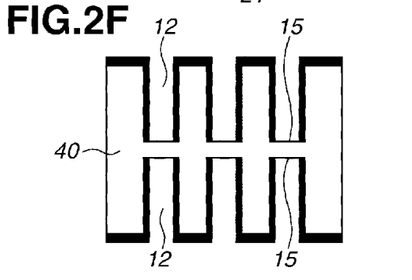

Next, the Si exposed surfaces are formed by at least partially removing the second insulating films formed on the bottoms of the Si recessed portions on the front surface and the back surface of the Si substrate (fifth process). As illustrated in FIG. 2F, the Si exposed surface 15 is formed by at least partially removing the second insulating film 34 formed on the bottom 14 of the Si recessed portion 12. This process is performed for each of the Si recessed portions on the front surface and the back surface. The method of partially removing the second insulating film 34 may be similar to the method of removing the second insulating film 34 in the first exemplary embodiment as illustrated in FIG. 1E. Execution of the above-described processes illustrated in FIGS. 2A to 2F results in the formation of the Si molds 40 on the both surfaces of the substrate, which are constituted by the Si recessed portions for plating of Si microstructures.

Figure 2G:
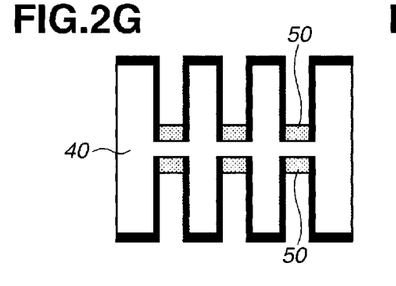
Figure 2H:
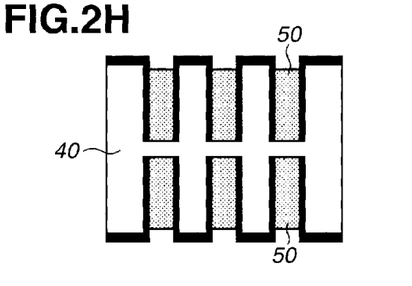

Next, metal microstructures are formed by filling the Si recessed portions with metals from the Si exposed surfaces on the front surface and the back surface of the Si substrate by electrolytic plating (sixth process). As illustrated in FIGS. 2G and 2H, the metal microstructures 50 are formed on the both surfaces of the Si substrate by electrolytic plating the insides 12 of the Si recessed portions with metals from the Si exposed surfaces 15 while using the Si molds 40 as molds. The metal electrolytic plating method may be similar to the metal electrolytic plating method in the first exemplary embodiment as illustrated in FIG. 1F.

According to the present exemplary embodiment, it is possible to manufacture a metal structure having a high aspect ratio on each of the both surfaces of an Si substrate. This is effective in many applications. For example, in the case of an X-ray absorption grating, the present exemplary embodiment can provide, as a total effect, an X-ray absorption effect substantially corresponding to a simple sum of the absorption effects of the metal microstructures on the front surface and the back surface. In other words, formation of metal microstructures on the both surfaces of an Si substrate enables the metal microstructure to have an aspect ratio corresponding to the sum of the aspect ratios of the metal microstructures on the front surface and the back surface. For example, if metal microstructures on the front surface and the back surface are substantially the same, the collective metal microstructure has an overall aspect ratio approximately twice compared to a metal microstructure having the microstructure formation only on one surface.

Further, the plating is carried out simultaneously from the both surfaces of the mold, whereby the time required for plating can be significantly reduced compared to plating performed for one surface at a time. Another effect of the present exemplary embodiment is improvement of the processing accuracy. In this method, the processing accuracy of a metal microstructure is generally determined based on an Si microstructure. Since the processing of an Si microstructure is substantially similar to the processing of an Si microstructure only on one surface, the processing accuracy is also substantially similar to the processing accuracy of an Si microstructure only on one surface. Further, even if a metal structure has an aspect ratio enabling the one-side formation, it is possible to reduce the processing difficulty and improve the processing accuracy by employing the formation on the both surfaces. An increase in the processing difficulty and a reduction in the processing accuracy first occur when a Si microstructure mold with a high aspect ratio is formed, and are more noticeable as an aspect ratio becomes higher. Especially, a structure having an aspect ratio of 50 or more often raises problems such as disarray and tilt of the Si microstructure, thereby resulting in strict processing conditions and a reduction in the processing rate.

In plating of an Si microstructure mold with a metal, a higher aspect ratio leads to difficulty in the entry of a plating solution into the bottom of the Si recessed portion, and bad circulation of the plating solution within the recessed portion. As a result, the plating should be carried out at a reduced plating rate, thereby deteriorating the productivity. Further, a higher aspect ratio may lead to uneven application of plating in the Si recessed portion and generation of voids in the metal structure. The present exemplary embodiment is highly effective for solving the above-described problems. According to the present exemplary embodiment, it is possible to comparatively easily manufacture a metal micro grating structure having a high aspect ratio of approximately 200 with a high degree of submicron precision.

Figure 3A:
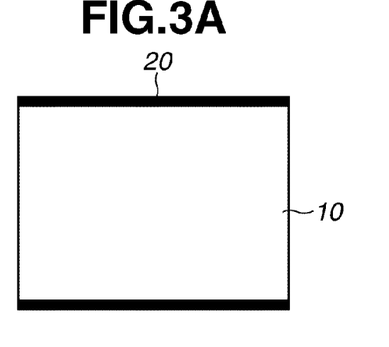
FIGS. 3A to 3J illustrate a microstructure manufacturing method according to a third exemplary embodiment of the present invention.
Figure 3B:
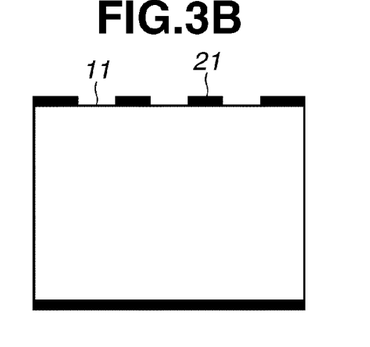
Figure 3C:
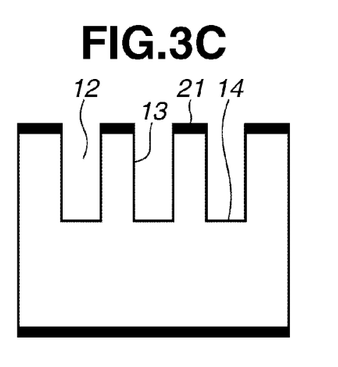
Figure 3D:
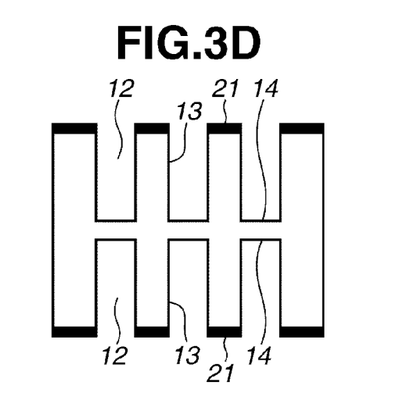
Figure 3E:
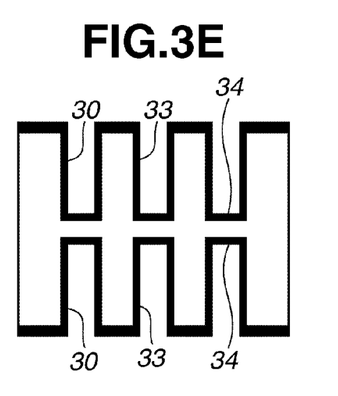

FIGS. 3A to 3B illustrates a third exemplary embodiment according to the microstructure manufacturing method of the present invention. The third exemplary embodiment is a method including forming an Si mold by penetratingly connecting the microstructures formed on the both surfaces of the Si substrate, and forming a metal microstructure by electrolytically plating the inside of the Si mold.

More specifically, by etching of the Si substrate from the exposed Si surfaces while using the first insulation films on the front surface and the back surface of the Si substrate as masks, the Si recessed portions on the front surface and the back surface of the Si substrate can be formed either in a manner that the respective Si recessed portions penetrate or in a manner that the respective Si recessed portions do not penetrate. The present exemplary embodiment employs the method that the Si recessed portions are formed in a manner that the respective Si recessed portions penetrate. In this method, a part of the bottom and/or a part of the sidewall of the Si recessed portion can serve as the Si exposed surface.

Figure 3F:
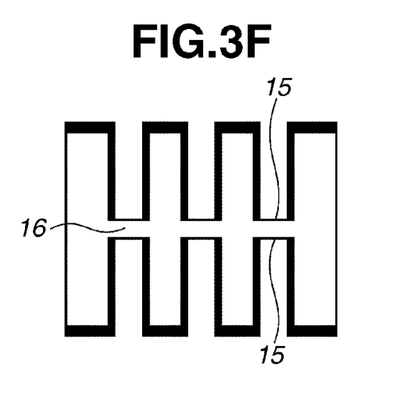
Figure 3G:
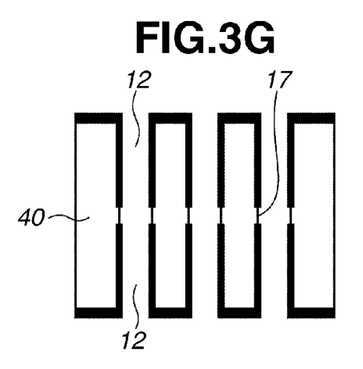

First, as illustrated in FIGS. 3A to 3G, the Si substrate 10 is processed so as to have the Si recessed portion which serves as the Si mold 40. The processes illustrated in FIGS. 3A to 3F may be similar to the processes in the second exemplary embodiment as illustrated in FIGS. 2A to 2F. In the present exemplary embodiment, the Si substrate 10 in the state illustrated in the FIG. 3F is processed so that the intermediate layer 16 defined between the Si recessed portions on the front and back surfaces is at least partially removed to penetratingly connect the Si recessed portions on the front and back surfaces, as illustrated in FIG. 3G. This processing results in the formation of the exposed surface 17 on the sidewall of the Si recessed portion. The removal of the Si intermediate layer 16 here may be performed in a similar manner to the removal in the first exemplary embodiment as illustrated in FIG. 1C. Execution of the processes illustrated in FIGS. 3A to 3G results in the formation of the Si mold 40 including the penetrating Si recessed portion.

Figure 3H:
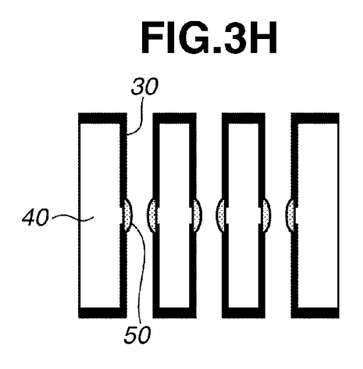
Figure 3I:
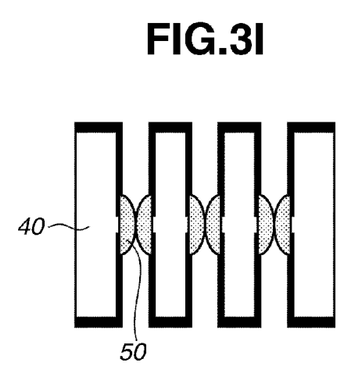
Figure 3J:
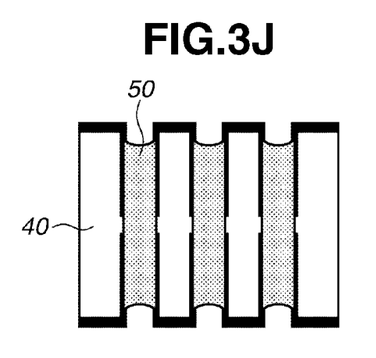

Next, as illustrated in FIGS. 3H to 3J, the metal microstructure 50 is manufactured by electrolytically plating the inside 12 of the Si structure with a metal from the Si exposed surface 17 while using the Si mold 40 including the penetrating Si recessed portion. The metal electrolytic plating method may be substantially similar to the metal electrolytic plating method in the first and second exemplary embodiments, except for a difference which will be now described. First, unlike the first and second exemplary embodiments, the present exemplary embodiment includes the penetrating Si microstructure constituted by the Si recessed portion, and the Si exposed surface 17 formed mainly on the sidewall of the recessed portion of the Si microstructure. Therefore, during electrolytic plating of a metal, the metal is deposited only on the Si exposed surface 17 in initial stage, as illustrated in FIG. 3H. After a while, the passage of the plating solution in the Si microstructure is closed by the deposited metal 50, as illustrated in FIG. 3I. Then, the metal plating is continued to form the desired metal microstructure 50, as illustrated in FIG. 3J.

According to the present exemplary embodiment, it is possible to manufacture a metal microstructure having a high aspect ratio in the penetrated Si mold. In this case, the following effects can be provided in addition to the effects of the second exemplary embodiment. The penetration of the Si microstructure results in the improvement of the circulation of the plating solution within the Si microstructure constituted by the Si recessed portion, compared to the plating without penetration of the Si microstructure. Therefore, it is possible to further facilitate the plating within the Si microstructure. Especially, it is possible to speed up the formation of a plating core in an early stage of plating. This state is maintained until the passage in the Si microstructure is closed by the metal 50 (FIG. 3I). Further, since the metal microstructure manufactured by the present exemplary embodiment has an integrated structure, it can provide more excellent element characteristics.

In a first example, as illustrated in FIGS. 1A to 1G, an Si microstructure was formed on one surface of an Si substrate, and an Au microstructure was formed by electrolytically plating the inside of the Si microstructure while using the Si microstructure as a mold. First, as illustrated in FIG. 1A, the first insulating film 20 was formed on the Si substrate 10. The Si substrate had a diameter of 100 mmφ, a thickness of 400 μm, and a resistivity of 0.02 Ωcm. The material of the first insulating film 20 was $SiO_2$. The wet thermal oxidation method was employed as the $SiO_2$ film formation method. The $SiO_2$ film with a thickness of approximately 1.2 μm was formed on each of the front surface and the back surface of the Si substrate 10 by thermal oxidation performed at 1050° C. for four hours. The resistivity of the $SiO_2$ film was 1000 Ωcm or more.

Figure 4A:
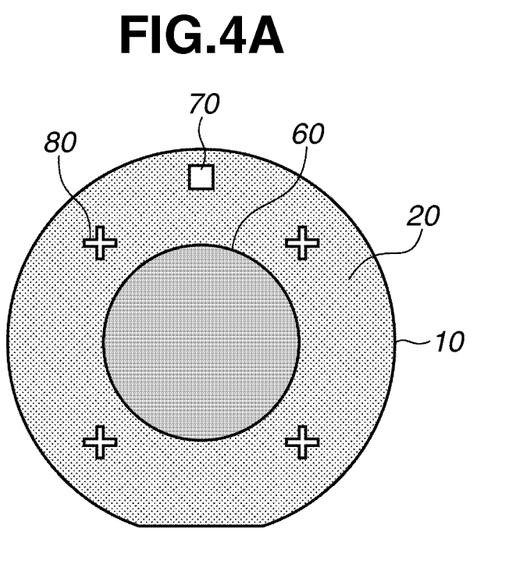
FIG. 4A illustrates a typical substrate (wafer) according to exemplary embodiment of the present invention.
Figure 4B:
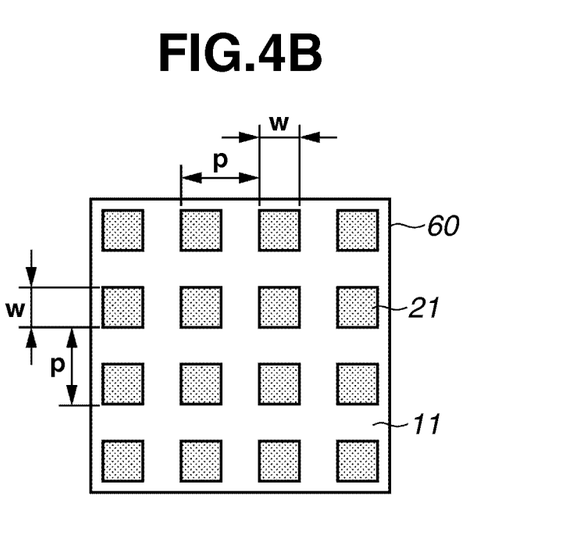
FIG. 4B illustrates a pattern on the substrate according to the exemplary embodiment of the present invention.

Next, as illustrated in FIG. 1B, the mask pattern 21 was formed by removing a part of the above-described first insulating film $SiO_2$, and at the same time, the surface of the Si substrate 10 was partially exposed to form the Si surface 11 portion. More specifically, first, a Cr film with a thickness of 100 nm was deposited on the $SiO_2$ as a metal film by the vacuum deposition method. Then, AZ1500 with a thickness of approximately 3 μm was applied on the Cr film as a photoresist. After that, the photoresist was exposed to light to form a desired pattern. As illustrated in FIG. 4A, the pattern 60 was disposed at approximately the center of the front surface of the substrate 10, and the diameter thereof was approximately 50 mmφ. As illustrated in FIG. 4B, the pattern was a periodic structure, and was an array of squares 4 μm on a side (W=4 μm) at 8 μm intervals (p=8 μm).

Next, the photoresist pattern was transformed onto the Cr by etching the Cr with use of a commercially available Cr etching solution. Then, the $SiO_2$ was etched by the $CHF_3$ plasma dry etching method with use of the Cr pattern as a mask to expose the Si surface portion 11. After that, the Cr film was all removed with use of the above-described etching solution, as a result of which the Si substrate 10 was covered with the $SiO_2$ pattern 21 while the surface portion 11 of the Si substrate 10 was exposed as illustrated in FIG. 4B. At this time, as illustrated in FIG. 4A, a square pattern approximately 1 mm on a side was formed at the periphery of the substrate 10 concurrently so that the electric pad 70 was formed.

Next, as illustrated in FIG. 1C, the Si substrate 10 was processed, with use of the $SiO_2$ pattern 21 as a mask, to form an array structure constituted by Si square poles. The method for processing the Si substrate 10 was the Bosch process RIE method, which alternately repeats etching with use of $SF_6$ gas and sidewall protective film deposition with use of $C_4F_8$ gas. After the execution of Bosch process RIE, the substrate was cleaned with a hydro fluoro ether (HFE) solution and a mixed solution of sulfuric acid and hydrogen peroxide for removing the sidewall protective film.

A cross-sectional observation of the Si structure with a scanning electron microscope (SEM) revealed that the height of the Si square pole was approximately 240 μm. Further, a research of the cross-sectional shape of the Si square pole after cutting the Si square pole with focused ion beam (FIB) revealed that the Si square pole was nearly square in cross-section. Although the Si square was approximately 4 μm on a side near the surface of the recessed portion, the Si square was approximately 3.6 μm on a side near the bottom of the recessed portion. Therefore, the obtained Si square pole had an aspect ratio of approximately 60. Further, an SEM cross-sectional observation revealed that the $SiO_2$ film 21 with a thickness of 0.2 μm or more remained on the Si square pole.

Next, as illustrated in FIG. 1D, the second insulating film 30 was formed on the sidewall 13 and the bottom 14 of the Si recessed portion 12 formed by the previous processing. In this example, $SiO_2$ was selected for the second insulating film 30, too. The film thickness of the second insulating film 30 was approximately 100 nm. The method for forming the second insulating film 30 was thermal oxidation as illustrated in FIG. 1A. The preferable feature of thermal oxidation is that it enables the formation of a highly dense $SiO_2$ film with a comparatively even thickness. This processing causes thermal oxidation to progress even at the portions other than the sidewall 13 and the bottom 14, i.e., the substrate top 21 covered with the $SiO_2$ film or the back surface of the substrate, and provides an increase in the film thickness of the $SiO_2$ film. This is advantageous to the later processes.

Next, as illustrated in FIG. 1E, the $SiO_2$ film 34 formed on the bottom 14 of the Si recessed portion 12 was removed to form the Si exposed surface 15. The partial removal of the $SiO_2$ film 34 was carried out by the dry etching method with use of $CHF_3$ plasma. This etching has high anisotropy and progresses nearly vertically relative to a substrate. Therefore, while the $SiO_2$ film 34 at the bottom was completely removed, the $SiO_2$ film on the sidewall remained so that Si of the sidewall was prevented from being exposed. On the other hand, the thickness of the $SiO_2$ film 21 on the substrate top was increased compared to the thickness of the film at the time of FIG. 1C which was 0.2 μm or more due to the thermal oxidation illustrated in FIG. 1D, as a result of which the $SiO_2$ film 21 remained even though the $SiO_2$ film 34 was completely removed so that the Si surface was prevented from being exposed at this portion. The above-described processes led to the formation of the Si mold 40 for plating, which had an Si exposed surface only at the bottom of the recessed portion while the other portions were covered with the $SiO_2$ film of a high resistivity.

Next, as illustrated in FIG. 1F, the Au microstructure 50 was formed by electrolytically plating the inside 12 of the Si structure with Au from the Si exposed surface 15 while using the portion 40 as a mold. Microfab Au1101 (manufacturer: Electroplating Engineers of Japan Ltd.) was used as an Au plating solution. At the time of the plating, the temperature of the plating solution was maintained at 60° C., and the current density was set to 0.2 A/dm². The plating solution was stirred to ensure even application of plating. The Si exposed surface 70 illustrated in FIG. 4A was utilized as an electrode pad for the mold side for the electrolytic plating.

The Si mold 40 had an exposed surface at the bottom of the Si recessed portion indicated as the Si exposed surface 15, and the other portions of the Si mold 40 were entirely covered with the $SiO_2$ film which was an insulating film. Therefore, at the time of the electrolytic plating of Au, Au was deposited only on the Si exposure surface 15 to form a dense Au microstructure within the recessed portion 12 of the Si mold 40.

The height of the Au microstructure 50 was controlled by the plating time so as to become approximately 200 μm. In other words, the aspect ratio of the obtained Au microstructure was approximately 50. A cross-sectional observation with, for example, a SEM revealed that the Au microstructure was dense and had no void. Further, an evaluation with an X-ray microscope confirmed that a grating image with clear contrast could be obtained, and the Au microstructure could absorb X-ray.

As indicated by the present example, element technologies required for the first exemplary embodiment are all derived from the well-known MEMS technology, and therefore can be readily carried out. Especially, the first exemplary embodiment employs the idea of using a highly processible Si substrate as a mold and enabling Au to be deposited only from the conductive bottom of the recessed portion of the mold by covering the surface of the mold with an insulating SiO$_2$ film, whereby it is possible to manufacture a metal micro grating structure having a high aspect ratio with a reduced number of manufacturing processes with a high degree of submicron precision. Further, the first exemplary embodiment uses an SiO$_2$ film which can prevent unnecessary Au deposition to, for example, the sidewall of the mold, and improve the selectivity of a plating solution for the Au plating.

In a second example, as illustrated in FIGS. 2A to 2H, Si microstructures were formed on the both surfaces of the Si substrate, and Au microstructures were manufactured by electrolytically plating the insides of the Si microstructures while using the Si microstructures as molds. First, as illustrated in FIGS. 2A to 2C, an Si microstructure was formed on the front surface of the Si substrate 10. The formation method thereof may be similar to the method in the first exemplary embodiment as illustrated by FIGS. 1A to 1C, and only a difference from the first exemplary embodiment will be described below.

The Si substrate had a diameter of 100 mmφ, a thickness of 300 μm and a resistivity of 0.02 Ωcm. The formed pattern of the Si microstructure was a line and space (L/S) structure having a pitch p=6 μm and a width w=3 μm. The depth of the recessed portion of the Si microstructure was approximately 130 μm. The recessed portion had a width of approximately 3 μm near the front surface and a width of approximately 2.8 μm near the bottom. Therefore, the aspect ratio of the obtained Si groove (recessed portion) was approximately 43. At this point, position alignment marks 80 were formed concurrently as illustrated in FIG. 4A, for the positioning of the Si microstructure on the back surface during the subsequent Si back surface processing.

Next, as illustrated in FIG. 2D, the shape corresponding to the Si structure formed on the front surface of the Si substrate 10 was formed on the back surface of the Si substrate 10 in a substantially mirror-symmetrical manner by applying processing from the back surface. The Si microstructure on the back surface had a nearly similar shape to the shape of the Si microstructure on the front surface, and was positioned with use of the position alignment marks 80 on the front surface of the Si substrate. The Si groove (recessed portion) on the back surface also had a depth of approximately 130 μm and an aspect ratio of approximately 43. The thickness of the layer 16 remaining between the Si microstructures on the front and back surfaces was approximately 40 μm.

Next, as illustrated in FIG. 2E, SiO$_2$ films having a thickness of approximately 50 nm were formed as second insulating films by heat oxidation on the sidewalls 13 and the bottoms 14 of the Si recessed portions 12 formed by the previous processing. The heat oxidation method enabled the SiO$_2$ films to be formed concurrently and evenly in the Si microstructures on the front and back surfaces. At this time, the thermal oxidation also progressed even at the portions of the substrate covered with the SiO$_2$ films, which increases the film thickness of the SiO$_2$ films.

Next, as illustrated in FIG. 2F, the SiO$_2$ film 34 formed on the bottom 14 of the Si recessed portion 12 was selectively removed, forming the Si exposed surface 15. This process was performed for each of the Si microstructures on the front and back surfaces. The method for partially removing the SiO$_2$ film 34 may be similar to the partially removing method in the first example as illustrated in FIG. 1E, and therefore the detailed description thereof will be omitted here. The execution of the above-described processes illustrated in FIGS. 2A to 2F led to the formation of the Si mold 40 for plating having the Si microstructures on the both surfaces of the substrate.

Next, as illustrated in FIGS. 2G to 2H, the metal microstructures 50 were formed on the both surfaces of the Si substrate by electrolytically plating the insides 12 of the Si structures with Au from the Si exposed surfaces 15 while using the Si molds 40 as molds. The metal electrolytic plating method may be similar to the metal electrolytic plating method in the first example as illustrated in FIG. F, and therefore the detailed description thereof will be omitted here. The heights of the Au microstructures 50 formed in the Si microstructures on the front and back surfaces were controlled by the plating time so as to become approximately 120 μm, respectively. In other words, the aspect ratios of the obtained Au microstructures on the front and back surfaces were approximately 43 respectively, and were approximately 86 in total. A cross-sectional observation with, for example, a SEM revealed that the Au microstructures were dense and had no void. Further, an evaluation with an X-ray microscope confirmed that a grating image with clear contrast could be obtained, and the Au microstructures could absorb X-ray.

As indicated by the present example, the second exemplary embodiment can manufacture high aspect ratio metal structures on the both surfaces of an Si substrate concurrently. This feature can provide not only the effect of a significant reduction in the time required for the manufacturing but also the effect of considerable improvement of the processing accuracy.

In a third example, as illustrated in FIGS. 3A to 3J, the Si mold was prepared through a penetrating connection between the microstructures formed on the both surfaces of the Si substrate, and an Au microstructure was manufactured by electrolytically plating the inside of the Si mold. First, as illustrated in FIGS. 3A to 3G, the Si substrate 10 was processed so that the Si microstructures were formed and the Si mold 40 was prepared. The processes illustrated in FIGS. 3A to 3F may be similar to the processes in the second example as illustrated in FIGS. 2A to 2F, and therefore the detailed descriptions thereof will be omitted here.

In the present example, the Si substrate 10 in the state illustrated in FIG. 3F was processed so that the intermediate layer 16 defined between the Si microstructures on the front and back surfaces was removed to penetratingly connect the Si microstructures on the front and back surfaces, as illustrated in FIG. 3G. This process forms the exposed surface 17 on the sidewall of the Si microstructure. This removal of the Si intermediate layer 16 may be performed in a similar manner to the Si etching method in the first example as illustrated in FIG. 1C. After the removal of the Si intermediate layer 16, the substrate was cleaned so that the Si surface could be sufficiently exposed at the exposed surface 17. The processes illustrated in FIGS. 3A to 3G resulted in the formation of the Si mold 40 including the penetrating Si microstructure. Here, the depth of the Si groove (recessed portion) was the same as the thickness of the Si substrate, and therefore was 300 μm. In other words, the aspect ratio of the Si groove (recessed portion) was approximately 100.

Next, as illustrated in FIGS. 3H to 3J, the Au microstructure 50 was formed by electrolytically plating the inside 12 of the Si structure with Au from the Si exposed surface 17 while using the Si mold 40 including the penetrating Si microstructure. The Au electrolytic plating method may be substantially similar to the electrolytic plating method in the first example and the second example, except for a difference which will be now described. In the present example, the Si microstructure was formed to penetrate and the Si exposed surface 17 was mainly formed on the sidewall of the recessed portion of the Si microstructure. Therefore, in the electrolytic plating of Au, the metal was deposited only on the Si exposed surface 17 in an early stage, as illustrated in FIG. 3H. In other words, the plating solution could pass through the through-hole of the Si microstructure until the deposited Au 50 closed the passage in the Si microstructure as illustrated in FIG. 3I. Due to this feature, the present example had excellent circulation of the plating solution inside the Si microstructure, and therefore was able to provide improved plating efficiency compared to the first and second examples.

Then, as illustrated in FIG. 3J, the Au plating was continued until the thickness of the Au microstructure 50 was increased to approximately 210 μm. In other words, the present example resulted in the formation of an Au microstructure having an aspect ratio of approximately 70. A cross-sectional observation with, for example, a SEM revealed that the Au microstructure was dense and had no void. Further, an evaluation with an X-ray microscope confirmed that a grating image with clear contrast could be obtained, and the Au microstructure could absorb X-ray.

As indicated by the present example, the third exemplary embodiment enables the formation of an Au microstructure having a high aspect ratio with use of the penetrating Si mold. Further, the third exemplary embodiment can provide the following effects in addition to the effects of the first and second examples. First, due to the penetration of the Si microstructure, it is possible to further speed up the formation of a plating core in an early stage of the plating, thereby improving the plating efficiency. Secondly, it is possible to integrate the golden microstructure without the intermediate layer 16 therebetween which exists in the second example. Due to this feature, higher applicability can be expected.

Figure 5A:
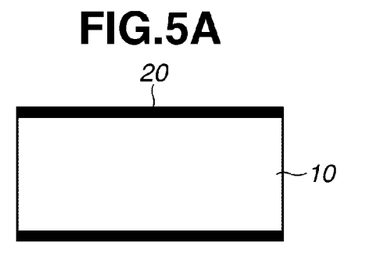
FIGS. 5A to 5G illustrate a fourth exemplary embodiment of the microstructure manufacturing method of the present invention.
Figure 5B:
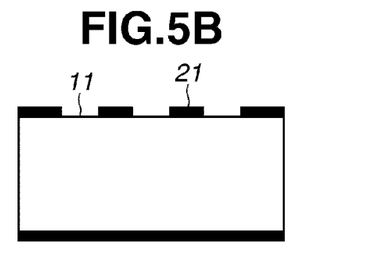

A fourth example will be described with reference to FIGS. 5A to 5G. The fourth example used the Si substrate 10 with a diameter of 100 mmφ, a thickness of 400 μm, and a resistivity of 0.02 Ωcm. Thermally oxidized films with a thickness of approximately 1.0 μm were respectively formed on the front surface and the back surface of the Si substrate 10 as the first insulating films 20 by applying thermal oxidation to the Si substrate 10 at 1050° C. for four hours (FIG. 5A). A chrome film with a thickness of 200 nm was formed on only one surface of the Si substrate 10 by an electron beam evaporation apparatus. A positive type photoresist was applied thereon, and patterning was performed by semiconductor photolithography in such a manner that a square resist pattern 4 μm on a side was two-dimensionally arranged at an 8 μm intervals in an square area 50 mm on a side. After that, the chrome was etched with use of a chrome etching solution, and subsequently, the thermally oxidized film was etched by the reactive etching method with use of $CHF_3$ to forma Si exposed surface around the resist pattern constituted by the pattern 4 μm on a side two-dimensionally arranged at the 8 μm interval (FIG. 5B).

Figure 5C:
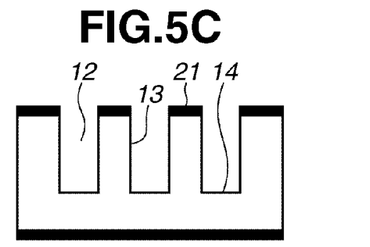

Next, as illustrated in FIG. 5C, anisotropic deep etching was applied to the Si exposed surface by the inductive coupled plasma-reactive ion etching (ICP-RIE) method. The deep etching was stopped when the deep etching progressed to 70 μm to form a two-dimensional grating composed of Si with a height of 70 μm. Subsequently, the resist and chrome were removed by ultraviolet (UV) ozone asking and a chrome etching solution. Further, the substrate was cleaned with use of a hydro fluoro ether solution and a mixed solution of sulfuric acid and hydrogen peroxide.

Figure 5D:
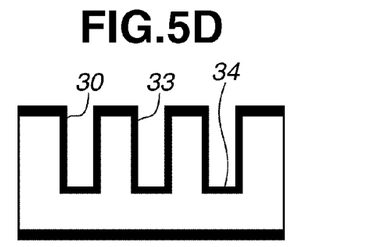
Figure 5E:
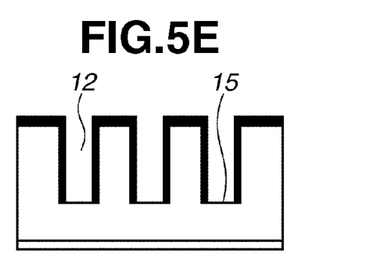

Next, as illustrated in FIG. 5D, a thermally oxidized film with a thickness of approximately 0.15 μm was formed as the second insulating film 30 by applying thermal oxidation at 1050° C. for 15 minutes, on the sidewall 13 of the Si recessed portion formed by the above-mentioned etching. Then, as illustrated in FIG. 5E, the thermally oxidized film formed on the bottom 14 of the Si recessed portion was removed to form the Si exposed surface 15. The partial removal of the thermally oxidized film was performed by the dry etching method with use of $CHF_3$ plasma. This etching has high anisotropy and progresses nearly vertically relative to a substrate. Therefore, while the thermally oxidized film 34 at the bottom of the Si recessed portion was completely removed, the thermally oxidized film 33 on the sidewall of the Si recessed portion remained so that the Si surface of the sidewall was prevented from being exposed.

Figure 5F:
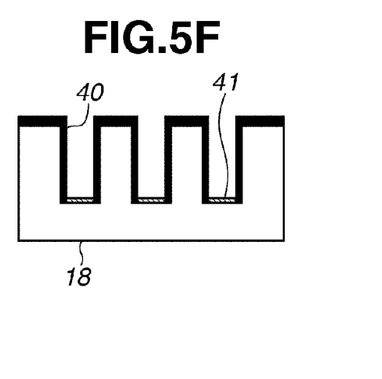

Next, a chrome film with a thickness of approximately 7.5 nm and a golden film with a thickness of approximately 55 nm were formed sequentially in this order by an electron beam evaporation apparatus. This processing resulted in the application of a metal film 41 composed of chrome and gold on the Si exposed surface 15 as illustrated in FIG. 5F, which further facilitates generation of a plating core.

Then, the thermally oxidized film formed on the back side of the surface processed by the above-described etching was removed by the dry etching method with use of $CHF_3$-plasma so that the Si surface was exposed. In the present example, this was used as the mold 40.

Figure 5G:
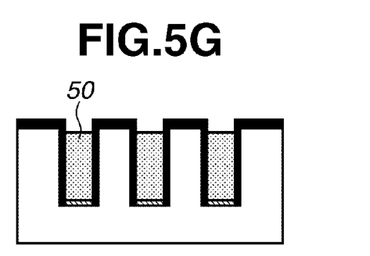

Next, as illustrated in FIG. 5G, golden plating was applied by energization through the exposed back side 18 of the Si substrate, as a result of which the metal microstructure 50 was formed. The golden plating was carried out with use non-cyanide gold plating solution (Microfab Au1101: Electroplating Engineers of Japan Ltd.) at 60° C. as the temperature of the plating solution at a current density of 0.2 $A/Dm^2$ for 8 hours. This plating resulted in the formation of the metal microstructure 50 made of gold with a thickness of approximately 50 μm. A cross-sectional observation with a SEM revealed that the metal microstructure 50 made of gold was dense, had no void, and had an even height. Further, an evaluation with an X-ray microscope confirmed that a grating image with clear contrast could be obtained, and the metal microstructure 50 made of gold could absorb X-ray.

Next, a fifth example will be described with reference to FIGS. 5A to 5G. The fifth example used the Si substrate 10 with a diameter of 100 mmφ, a thickness of 400 μm, and a resistivity of 0.02 Ωcm. Thermally oxidized films with a thickness of approximately 1.0 μm were respectively formed on the front surface and the back surface of the Si substrate 10 as the first insulating films 20 by applying thermal oxidation to the Si substrate 10 at 1050° C. for four hours (FIG. 5A). A chrome film with a thickness of 200 nm was formed on only one surface of the Si substrate 10 by an electron beam evaporation apparatus. A positive type photoresist was applied thereon, and patterning was performed by semiconductor photolithography in such a manner that a square resist pattern 2 μm on a side was two-dimensionally arranged at 4 μm intervals in a square area 50 mm on a side. After that, the chrome was etched with use of a chrome etching solution, and subsequently, the thermally oxidized film was etched by the reactive etching method with use of $CHF_3$. As a result, a Si exposed surface was formed around the resist pattern constituted by the pattern 2 µm on a side two-dimensionally arranged at the 4 µm intervals (FIG. 5B).

Next, as illustrated in FIG. 5C, anisotropic deep etching was applied to the exposed Si surface by the ICP-RIE method. The deep etching was stopped when the deep etching progressed to 70 µm. This resulted in the formation of a two-dimensional grating composed of Si with a height of 70 µm. Subsequently, the resist and chrome were removed by UV ozone asking and a chrome etching solution. Further, the substrate was cleaned with use of a hydro fluoro ether solution and a mixed solution of sulfuric acid and hydrogen peroxide. After the substrate was washed with water, the substrate was immersed in isopropyl alcohol, and then was dried by supercritical drying with use of supercritical carbon dioxide.

Next, as illustrated in FIG. 5D, a thermally oxidized film with a thickness of approximately 0.15 µm was formed as the second insulating film 30 by applying thermal oxidation at 1050° C. for 15 minutes, on the sidewall 13 of the Si recessed portion formed by the above-mentioned etching. Then, as illustrated in FIG. 5E, the thermally oxidized film formed on the bottom 14 of the Si recessed portion was removed, as a result of which the Si exposed surface 15 was formed. The partial removal of the thermally oxidized film was performed by the dry etching method with use of $CHF_3$ plasma. This etching has high anisotropy and progresses nearly vertically relative to a substrate. Therefore, while the thermally oxidized film 34 at the bottom of the Si recessed portion was completely removed, the thermally oxidized film 33 on the sidewall of the Si recessed portion remained so that the Si surface of the sidewall was prevented from being exposed.

Next, a chrome film with a thickness of approximately 7.5 nm and a copper film with a thickness of approximately 50 nm were formed sequentially in this order by an electron beam evaporation apparatus. This processing applies a metal film 41 composed of chrome and copper on the Si exposed surface 15 as illustrated in FIG. 5F. Since copper has a greater ionization tendency than gold, the copper surface on the bottom 14 of the Si recessed portion is displaced by gold when being immersed in a gold plating solution, which facilitates generation of a gold plating nucleus. Further, the copper slightly attached to the side wall 13 of the Si recessed portion at the time of electron beam evaporation is dissolved and removed. Therefore, development of the plating is facilitated on the bottom 14 of the Si recessed portion.

Then, the thermally oxidized film formed on the back side of the surface processed by the above-described etching was removed by the dry etching method with use of $CHF_3$-plasma so that the Si surface was exposed. In the present example, this was used as the mold 40.

Next, as illustrated in FIG. 5G, golden plating was applied by energization through the exposed back side 18 of the Si substrate, as a result of which the metal microstructure 50 was formed. The golden plating was carried out with use of a non-cyanide gold plating solution (Microfab Au1101: Electroplating Engineers of Japan Ltd.) at 60° C. as the temperature of the plating solution at a current density of 0.2 A/dm² for 8 hours. This plating forms the metal microstructure 50 made of gold with a thickness of approximately 50 µm. A cross-sectional observation with a SEM revealed that the metal microstructure 50 made of gold was dense, had no void, and had an even height, and further, the surface of the metal microstructure 50 in the Si recessed portion 12 was flat. Further, an evaluation with an X-ray microscope confirmed that a grating image with clear contrast could be obtained, and the metal microstructure 50 made of gold could absorb X-ray.

The microstructure manufacturing method according to the present example enables easy manufacturing of a metal microstructure having a high aspect ratio with a high degree of precision, and the resulting metal microstructure can be utilized for, for example, an X-ray absorption grating, an X-ray beam splitter, a photonic crystal, a metamaterial, and a metal mesh for a transmission electronic microscope.

Figure 6:
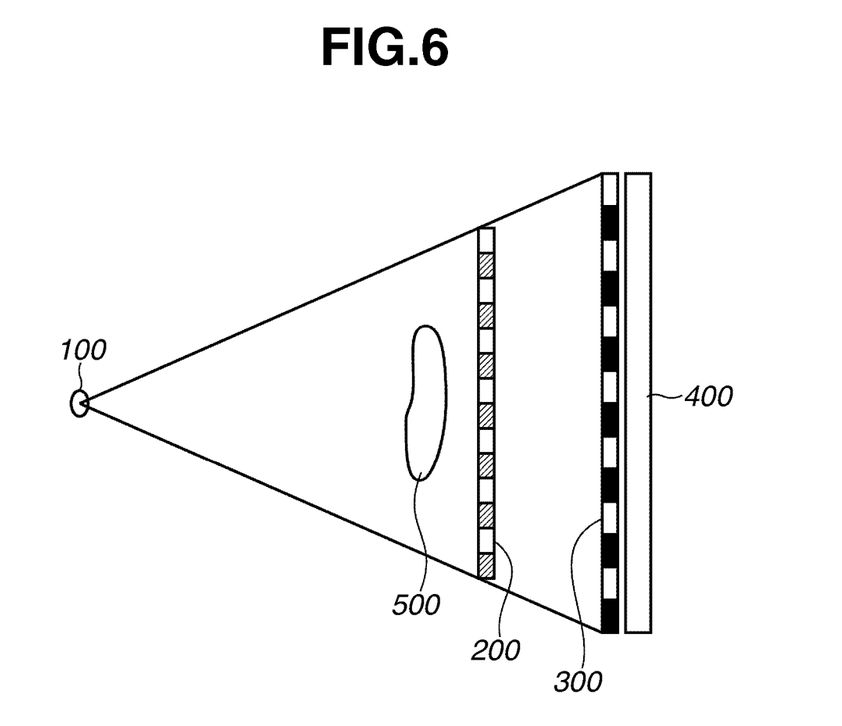
FIG. 6 illustrates a structure of an imaging apparatus according to the exemplary embodiments of the present invention.

In the following, an imaging apparatus utilizing the X-ray Talbot interference method will be described with reference to FIG. 6. FIG. 6 illustrates a configuration of an imaging apparatus using the microstructure manufactured in the above-described exemplary embodiments or examples as an X-ray absorption grating.

The imaging apparatus according to the present exemplary embodiments includes an X-ray source 100 for emitting spatially coherent X-ray, a diffraction grating 200 for periodically modulating the phase of the X-ray, an absorption grating 300 in which an X-ray absorption portion (shield portion) and a transmission portion are arranged, and a detector 400 for detecting the X-ray. The absorption grating 300 is the microstructure manufactured by the above-described exemplary embodiments or examples.

When a subject 500 is positioned between the X-ray source 100 and the diffraction grating 200, information about X-ray phase shift due to the subject 500 is detected as moire by the detector. In other words, this imaging apparatus captures an image of the subject 500 by imaging moire which holds phase information of the subject 500. Execution of phase retrieval processing such as Fourier transform based on this detection result enables a phase image of the subject to be obtained.

Since the imaging apparatus according to the present exemplary embodiments uses a less defective absorption grating, it can capture a phase image of a subject more accurately.

While the present invention has been described with reference to exemplary embodiments, it is to be understood that the invention is not limited to the disclosed exemplary embodiments. The scope of the following claims is to be accorded the broadest interpretation so as to encompass, for example, all substantially equivalent modifications, structures, and functions.

What is claimed is:

1. An X-ray absorption grating comprising:
an Si substrate including a recessed portion;
an insulating film provided on a sidewall of the recessed portion; and
a metal filled in the recessed portion to be in contact with the insulating film,
wherein a thickness of the insulating film is within a range of 5 nm to 5000 nm,
wherein the insulating film is not formed on at least a part of a bottom of the recessed portion, and
wherein the metal is in contact with an Si surface of the Si substrate at least on the part.

2. The X-ray absorption grating according to claim 1, wherein an aspect ratio of the metal is 5 to 100.

3. The X-ray absorption grating according to claim 1, wherein a plurality of protrusions, which is a part other than the recessed portion of the Si substrate, is located in the metal.

4. The X-ray absorption grating according to claim 1, wherein an outer periphery of the metal is a circle.

5. The X-ray absorption grating according to claim 1, wherein an outer periphery of the metal is a circle, and
wherein a plurality of protrusions, which is a part other than the recessed portion of the Si substrate, is located in the circle.

6. The X-ray absorption grating according to claim 1, wherein an outer periphery of the metal is a circle, and
wherein a plurality of protrusions, which is a part other than the recessed portion of the Si substrate, being aligned at constant intervals in a first direction is aligned at constant intervals in a second direction intersecting the first direction, in the circle.

7. The X-ray absorption grating according to claim 1, wherein the thickness of the insulating film is within a range of 10 nm to 1000 nm.

8. An X-ray Talbot interferometer comprising:
a diffraction grating for diffracting X-ray emitted from an X-ray source;
an absorption grating for absorbing a part of the X-ray diffracted by the diffraction grating, the absorption grating comprising,
an Si substrate with a plurality of recessed portions formed thereon, an insulating film provided on a sidewall of the recessed portions, and a metal filled in each of the plurality of recessed portions to be in contact with the insulating film,
the insulating film being not disposed on at least a part of a bottom of the recessed portion, the metal being in contact with an Si surface of the Si substrate on the at least part; and
a detector for detecting the X-ray which has passed through the absorption grating,
wherein a thickness of the insulating film is within a range of 5 nm to 5000 nm.

9. The X-ray Talbot interferometer according to claim 8, wherein an outer periphery of the metal of the absorption grating is a circle, and
wherein a plurality of protrusions, which is a part other than the recessed portion of the Si substrate, is located in the circle.

10. The X-ray Talbot interferometer according to claim 8, wherein the thickness of the insulating film is within a range of 10 nm to 1000 nm.

* * * * *